United States Patent
Cuenoud et al.

(10) Patent No.: US 7,622,484 B2
(45) Date of Patent: *Nov. 24, 2009

(54) MIXTURES OR ORGANIC COMPOUNDS FOR THE TREATMENT OF AIRWAY DISEASES

(75) Inventors: Bernard Cuenoud, Lausanne (CH); Robin A Fairhurst, Horsham (GB); Nicholas Lowther, Horsham (GB)

(73) Assignee: Novartis AG, Basel (CH)

( * ) Notice: Subject to any disclaimer, the term of this patent is extended or adjusted under 35 U.S.C. 154(b) by 138 days.

This patent is subject to a terminal disclaimer.

(21) Appl. No.: 11/248,462

(22) Filed: Oct. 12, 2005

(65) Prior Publication Data

US 2006/0052352 A1 Mar. 9, 2006

Related U.S. Application Data

(60) Division of application No. 10/911,201, filed on Aug. 4, 2004, now Pat. No. 7,008,951, which is a continuation of application No. 10/433,546, filed as application No. PCT/EP01/14122 on Dec. 3, 2001, now Pat. No. 6,800,643.

(30) Foreign Application Priority Data

Dec. 4, 2000 (GB) ................. 0029562.6

(51) Int. Cl.
*C07D 215/02* (2006.01)
*A61K 31/47* (2006.01)
(52) U.S. Cl. ...................... 514/312; 546/157
(58) Field of Classification Search ................. 514/312; 546/157
See application file for complete search history.

(56) References Cited

U.S. PATENT DOCUMENTS

| | | | |
|---|---|---|---|
| 4,607,028 A | 8/1986 | Schmidlin | 514/180 |
| 6,172,099 B1 | 1/2001 | Miyoshi et al. | 514/411 |
| 6,469,070 B1 | 10/2002 | Vanden Berghe | 514/738 |
| 6,537,524 B1 | 3/2003 | Hassan et al. | 424/45 |
| 6,664,235 B1 | 12/2003 | Kanie et al. | 514/25 |
| 6,800,643 B2 * | 10/2004 | Cuenoud et al. | 514/312 |
| 6,878,721 B1 * | 4/2005 | Cuenoud et al. | 514/312 |
| 7,008,951 B2 * | 3/2006 | Cuenoud et al. | 514/311 |
| 2005/0153957 A1 * | 7/2005 | Cuenoud et al. | 514/222.2 |

FOREIGN PATENT DOCUMENTS

| | | |
|---|---|---|
| EP | 0 135 476 | 3/1985 |
| EP | 0 882 704 | 12/1998 |
| JP | 09 309830 | 12/1997 |
| WO | 93/18007 | 9/1993 |
| WO | 95/25104 | 9/1995 |
| WO | 96/22764 | 8/1996 |
| WO | 00/75114 | 12/2000 |
| WO | WO 00/75144 | 12/2000 |

OTHER PUBLICATIONS

West, Anthony R., Solid State Chemistry and its Applications, Wiley, New York, 1988, pp. 358 & 365.*

* cited by examiner

*Primary Examiner*—Rita J Desai
(74) *Attorney, Agent, or Firm*—Cozette M McAvoy; Jennifer C Chapman

(57) ABSTRACT

A medicament comprising, separately or together, (A) a compound of formula (I) in free or pharmaceutically acceptable salt or solvate form and (B) a corticosteroid, for simultaneous, sequential or separate administration in the treatment of an inflammatory or obstructive airways disease, the molar ratio of (A) to (B) being from 100:1 to 1:300.

8 Claims, No Drawings

MIXTURES OR ORGANIC COMPOUNDS FOR THE TREATMENT OF AIRWAY DISEASES

This application is divisional of U.S. application Ser. No. 10/911,201, filed Aug. 4, 2004, which is a continuation of U.S. application Ser. No. 10/433,546, filed Jun. 4, 2003 which is a national stage application of PCT Patent Application No. PCT/EP01/14122, filed Dec. 3, 2001, which are herein incorporated by reference.

This invention relates to organic compounds and their use as pharmaceuticals, in particular for the treatment of inflammatory or obstructive airways diseases.

In one aspect, the present invention provides a medicament comprising, separately or together, (A) a compound of formula

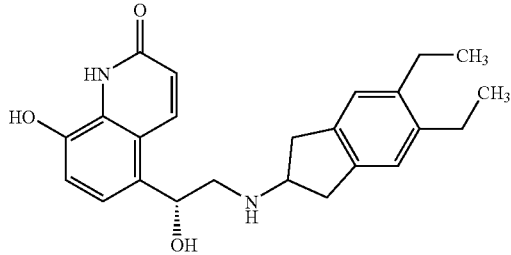

in free or pharmaceutically acceptable salt or solvate form and (B) a corticosteroid, for simultaneous, sequential or separate administration in the treatment of an inflammatory or obstructive airways disease.

In another aspect, the present invention provides a method of treating an inflammatory or obstructive airways disease which comprises administering to a subject in need of such treatment effective amounts of (A) as hereinbefore defined and (B) as hereinbefore defined.

In a further aspect, the present invention provides a pharamceutical composition comprising a mixture of effective amounts of (A) as hereinbefore defined and (B) as hereinbefore defined, optionally together with at least one pharmaceutically acceptable carrier.

The invention further provides the use of (A) as hereinbefore defined and/or (B) as hereinbefore defined in the preparation of a medicament for combination therapy by simultaneous, sequential or separate administration of (A) and (B) in the treatment of an inflammatory or obstructive airways disease.

The compound of formula I may be prepared in free or salt or solvate form by reacting (R)-8-benzyloxy-S-oxiranylcarbostyril with 5,6-diethylindan-2-ylamine to give 8-benzyloxy-5-[(R)-2-(5,6-diethyl-indan-2-ylamino)-1-hydroxyethyl]-1H-quinolin-2-one, subjecting the latter to a deprotecting reaction to replace the benzyl group by hydrogen, and recovering the resultant compound of formula I in free or salt or solvate form. The reactions may be carried out using the procedures hereinafter described in the Examples or analogous procedures. (R)-8-benzyloxy-S-oxiranylcarbostyril may be prepared as described in WO95/25104. 5,6-Diethylindan-2-ylamine may be prepared by known methods or analogues thereof, for example as described hereinafter in the Examples.

Pharmaceutically acceptable salts of the compound of formula I may be acid addition salts, including those of inorganic acids, for example hydrohalic acids such as hydrofluoric acid, hydrochloric acid, hydrobromic acid or hydriodic add, nitric acid, sulfuric acid, phosphoric acid; and organic acids such as formic acid, acetic acid, propionic acid, butyric acid, benzoic acid, o-hydroxybenzoic acid, p-hydroxybenzoic acid, p-chlorobenzoic acid, diphenylacetic acid, triphenylacetic acid, 1-hydroxynaphthalene-2-carboxylic acid, 3-hydroxynaphthalene-2-carboxylic acid alphatic hydroxy acids such as lactic acid, citric acid, tartaric acid or malic acid, dicarboxylic acids such as fumaric acid, maleic acid or succinc acid, and sulfonic acids such as methanesulfonic acid or benzenesulfonic acid. These salts may be prepared from compounds of formula I by known salt-forming procedures. Pharmaceutically acceptable solvates are generally hydrates. A particularly preferred form of the compound of Formula I is the maleate salt.

The corticosteroid (B) may be, for example, of formula

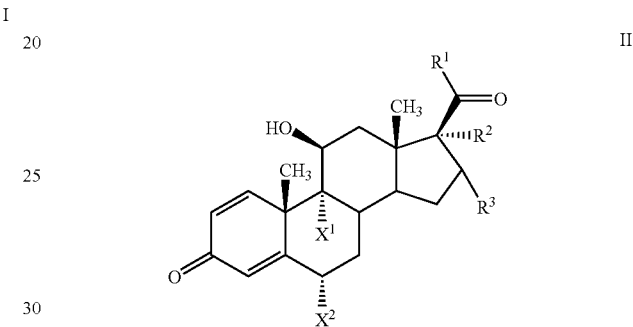

or a 1,2-dihydro derivative thereof, where $R^1$ is $C_1$-$C_4$-alkyl optionally substituted by halogen (preferably chlorine or fluorine), hydroxy, $C_1$-$C_4$-alkoxy, acyloxy or by acylthio, or $R^1$ is $C_1$-$C_4$-alkoxy or $C_1$-$C_4$-alkylthio optionally substituted by halogen, or $R^1$ is 5-or 6-membered heterocyclylthio, either $R^2$ is acyloxy and $R^3$ is hydrogen or $C_1$-$C_4$-alkyl, or $R^2$ and $R^3$ together denote a group of formula

where $R^4$ is $C_1$-$C_4$-alkyl or $C_3$-$C_6$-cycloalkyl and $R^5$ is hydrogen or $C_1$-$C_4$-alkyl, and $X^1$ and $X^2$ are each independently hydrogen, chlorine or fluorine.

$C_1$-$C_4$-alkyl as used herein may be methyl, ethyl, n-propyl, isopropyl, u-butyl, isobutyl, sec-butyl or tert-butyl.

$C_1$-$C_4$-alkoxy as used herein may be methoxy, ethoxy, n-propoxy, isopropoxy, n-butoxy, isobutoxy, sec-butoxy or tert-butoxy.

$C_1$-$C_4$-alkylthio as used herein may be methylthio, ethylthio, n-propylthio, isopropylthio, n-butylthio, isobutylthio, sec-butylthio or tert-butylthio.

When $R^1$ is acyloxy-substituted $C_1$-$C_4$-alkyl, the acyloxy group may be, for example, $C_1$-$C_{20}$-alkylcarbonyloxy, e.g. acetyloxy, n-propionyloxy, isopropionyloxy or hexadecanoyloxy, or $C_3$-$C_6$-cycloalkyltarbonyloxy, e.g. cyclohexylcarbonyloxy. When $R^1$ is acylthio-substituted $C_1$-$C_4$-alkyl, the acylthio group may be, for example, $C_1$-$C_4$-alkylcarbonylthio, e.g. acetylthio or n-propionylthio. When $R^1$ is 5-or-6- membered heterocyclylthio, the heterocyclyl group may be an O-heterocyclyl group, for example a furanonyl group.

When $R^2$ is acyloxy, it may be, for example, $C_1$-$C_4$-alkylcarbonyloxy, e.g. acetyloxy, n-propionyloxy, or n-butyroyloxy, $C_3$-$C_6$-cycloalkylcarbonyloxy e.g. cyclopropylcarbonyloxy, or 5-or 6-membered heterocyclylcarbonyloxy e.g. furoyloxy.

When $R^3$ is $C_1$-$C_4$-alkyl it may be in the alpha or beta conformation, more usually in the alpha conformation.

When $R^2$ and $R^3$ together denote a group of formula III, $R^4$ as $C_3$-$C_6$-cycloalkyl may be, for example, cyclohexyl.

Corticosteroids of formula I and their 1,2-dihydro derivatives include beclamethasone dipropionate, budesonide, fluticasone propionate, mometasone furoate, ciclesonide, triamcinolone acetonide, flunisolide, rofleponide palmitate, butixocort propionate and icometasone enbutate. In particularly preferred emodiments of the invention, the corticosteroid (B) is budesonide, fluticasone propionate or mometasone furoate.

Administration of the medicament or pharmaceutical composition as hereinbefore described, i.e. with (A) and (B) in admixture or separate, is preferably by inhalation, i.e. (A) and (B) or the mixture thereof are in inhalable form. The inhalable form of the medicament i.e. of (A) and/or (B) may be, for example, an atomizable composition such as an aerosol comprising the active ingredient, i.e. (A) and (B) separately or in admixture, in solution or dispersion in a propellant, or a nebulizable composition comprising a solution or dispersion of the active ingredient in an aqueous, organic or aqueous/organic medium. For example, the inhalable form of the medicament may be an aerosol comprising a mixture of (A) and (B) in solution or dispersion in a propellant, or a combination of an aerosol containing (A) in solution or dispersion in a propellant with an aerosol containing (B) in solution or dispersion in a propellant. In another example, the inhalable form is a nebulizable composition comprising a dispersion of (A) and (B) in an aqueous, organic or aqueous/organic medium, or a combination of a dispersion of (A) in such a medium with a dispersion of (B) in such a medium.

An aerosol composition suitable for use as the inhalable form of the medicament may comprise the active ingredient in solution or dispersion in a propellant, which may be chosen from any of the propellants known in the art. Suitable such propellants include hydrocarbons such as n-propane, n-butane or isobutane or mixtures of two or more such hydrocarbons, and halogen-substituted hydrocarbons, for example chlorine and/or fluorine-substituted methanes, ethanes, propanes, butanes, cyclopropanes or cyclobutanes, such as dichlorodifluoromethane (CFC 12), trichlorofluoromethane (CFC11), 1,2-dichloro-1,1,2,2-tetrafluoroethane (CFC114) or, particularly, 1,1,1,2-tetrafluoroethane (HFA134a) and 1,1,1,2,3,3,3-heptafluoropropane (HFA227), or mixtures of two or more such halogen-substituted hydrocarbons. Where the active ingredient is present in suspension in the propellant, i.e. where it is present in particulate form dispersed in the propellant, the aerosol composition may also contain a lubricant and a surfactant, which may be chosen from those lubricants and surfactants known in the art. Other suitable aerosol compositions include surfactant-free or substantially surfactant-free aerosol compositions. The aerosol composition may contain up to about 5% by weight, for example 0.0001 to 5%, 0.001 to 5%, 0.001 to 3%, 0.001 to 2%, 0.001 to 1%, 0.001 to 0.1%, or 0.001 to 0.01% by weight of the active ingredient, based on the weight of the propellant. Where present, the lubricant and surfactant may be in an amount up to 5% and 0.5% respectively by weight of the aerosol composition. The aerosol composition may also contain a co-solvent such as ethanol in an amount up to 30% by weight of the composition, particularly for administration from a pressurised metered dose inhalation device. The aerosol composition may further contain a bulking agent, for example a sugar such as lactose, sucrose, dextrose, mannitol or sorbitol, in an amount, for example, of up to 20%, usually 0.001 to 1%, by weight of the composition.

In another embodiment of the invention, the inhalable form is a dry powder, i.e. (A) and/or (B) are present in a dry powder comprising finely divided (A) and/or (B) optionally together with at least one particulate pharmaceutically acceptable carrier, which may be one or more materials known as pharmaceutically acceptable carriers, preferably chosen from materials known as carriers in dry powder inhalation compositions, for example saccharides, including monosaccharides, disaccharides, polysaccharides and sugar alcohols such as arabinose, glucose, fructose, ribose, mannose, sucrose, trehalose, lactose, maltose, starches, dextran, mannitol or sorbitol. An especially preferred carrier is lactose. The dry powder may be contained as unit doses in capsules of, for example, gelatin or plastic, or in blisters (e.g. of aluminium or plastic), for use in a dry powder inhalation device, which may be a single dose or multiple dose device, preferably in dosage units of (A) and/or (B) together with the carrier in amounts to bring the total weight of powder per capsule to from 5 mg to 50 mg. Alternatively, the dry powder may be contained in a reservoir in a multi-dose dry powder inhalation device adapted to deliver, for example, 3-25 mg of dry powder per actuation.

In the finely divided particulate form of the medicament, and in the aerosol composition where the active ingredient is present in particulate form, the active ingredient may have an average particle diameter of up to about 10 μm, for example 0.1 to 5 μm, preferably 1 to 5 μm. The particulate carrier, where present, generally has a maximum particle diameter up to 300 μm, preferably up to 212 μm, and conveniently has a mean particle diameter of 40 to 100 μm, e.g. 50 to 75 μm. The particle size of the active ingredient, and that of a particulate carrier where present in dry powder compositions, can be reduced to the desired level by conventional methods, for example by grinding in an airjet mill, ball mill or vibrator mill, sieving, microprecipitation, spray-drying, lyophilisation or controlled crystallisation from conventional solvents or from supercritical media.

The inhalable medicament may be administered using an inhalation device suitable for the inhalable form, such devices being well known in the art. Accordingly, the invention also provides a pharmaceutical product comprising a medicament or pharmaceutical composition as hereinbefore described in inhalable form as hereinbefore described in association with one or more inhalation devices. In a further aspect, the invention provides an inhalation device, or a pack of two or more inhalation devices, containing a medicament or pharmaceutical composition as hereinbefore described in inhalable form as hereinbefore described.

Where the inhalable form of the active ingredient is an aerosol composition, the inhalation device may be an aerosol vial provided with a valve adapted to deliver a metered dose, such as 10 to 100 μl, e.g. 25 to 50 μl, of the composition, i.e. a device known as a metered dose inhaler. Suitable such aerosol vials and procedures for containing within them aerosol compositions under pressure are well known to those skilled in the art of inhalation therapy. For example, an aerosol composition may be administered from a coated can, for example as described in EP-A-0642992. Where the inhalable form of the active ingredient is a nebulizable aqueous, organic or aqueous/organic dispersion, the inhalation device may be a known nebulizer, for example a conventional pneumatic nebulizer such as an airjet nebulizer, or an ultrasonic nebulizer, which may contain, for example, from 1 to 50 ml, commonly 1 to 10 ml, of the dispersion; or a hand-held nebulizer, sometimes referred to as a soft mist or soft spray inhaler, for example an electronically controlled device such as an AERx (Aradigm, US) or Aerodose (Aerogen), or a mechanical device such as a RESPIMAT (Boehringer Ingelheim) nebulizer which allows much smaller nebulized volumes, e.g. 10 to 100 µl, than conventional nebulizers. Where the inhalable form of the active ingredient is the finely divided particulate form, the inhalation device may be, for example, a dry powder inhalation device adapted to deliver dry powder from a capsule or blister containing a dry powder comprising a dosage unit of (A) and/or (B) or a multidose dry powder inhalation (MDPI) device adapted to deliver, for example, 3-25 mg of dry powder comprising a dosage unit of (A) and/or (B) per actuation. Suitable such dry powder inhalation devices are well known. For example, a suitable device for delivery of dry powder in-encapsulated form is that described in U.S. Pat. No. 3,991,761, while a suitable MDPI device is that described in WO97/20589.

The medicament of the invention is preferably a pharmaceutical composition comprising a mixture of (A) as hereinbefore defined and (B) as hereinbefore defined, preferably together with at least one pharmaceutically acceptable carrier as hereinbefore described.

The molar ratio of the compound (A) to the steroid (B) may be, in general, from 100:1 to 1:300, for example from 50:1 to 1:100 or from 20:1 to 1:50, preferably from 10:1 to 1:20, more preferably from 5:1 to 1:10, from 3:1 to 1:7 or from 2:1 to 1:2. The compound (A) and the steroid (B) may be administered separately in the same ratio.

A suitable daily dose of the compound (A), particularly as the maleate salt, for inhalation may be from 20 µg to 2000 µg, for example from 20 to 150 µg, from 20 to 1000 µg, preferably from 50 to 800 µg, e.g. from 100 to 600 µg or from 100 to 500 µg. A suitable daily dose of steriod (B) for inhalation may be from 20 µg to 5000 µg, for example from 20 to 4000 µg, from 50 to 3000 µg, from 50 to 2000 µg, from 50 to 1000 µg, from 50 to 500 µg, from 50 to 400 µg, from 50 to 300 µg, from 50 to 200 µg or from 50 to 100 µg. Where (B) is budesonide, a suitable daily dose may be from 25 to 4800 µg, for example from 25 to 4000 µg, from 25 to 3200 µg, from 25 to 2400 µg, from 25 to 1600 µg, from 50 to 4800 µg, from 50 to 4000 µg, from 50 to 3200 µg, from 50 to 2400 µg, from 50 to 1600 µg, from 100 to 4000 µg from 100 to 3200 µg, from 100 to 2400 µg, from 100 to 1600 µg, from 100 to 800 µg, from 100 to 400 µg, from 200 to 4000 µg, from 200 to 1600 µg, from 200 to 800 µg or from 200 to 400 µg, 100 to 1600 µg being preferred. Where (B) is mometasone furoate, a suitable daily dose may be from 50 µg to 2000 µg, for example from 100 to 200 µg, from 100 to 1600 µg, from 100 to 1000 µg or from 100 to 800 µg, preferably from 200 to 500 µg, for instance from 200 to 400 µg. Where (B), is fluticasone propionate, a suitable daily dose may be for inhalation may be from 25 to 2000 µg, for example from 25 to 1500 µg, from 25 to 1000 µg, from 25 to 500 µg, from 25 to 250 µg, from 50 to 1500 µg, from 50 to 1000 µg, from 50 to 500 µg, from 50 to 250 µg, from 100 to 1500 µg, from 100 to 1000 µg, from 100 to 500 µg, from 100 to 250 µg, from 200 to 1500 µg, from 200 to 1000 µg or from 200 to 500 µg, 100 to 1000 µg being preferred.

A suitable unit dose of compound (A), particularly as the maleate salt, may be from 20 to 2000 µg, for example from 20 to 1500 µg, from 20 to 1000 µg, preferably from 50 to 800 µg, from 50 to 600 µg or from 50 to 500 µg. A suitable unit dose of budesonide may be from 25 to 2400 µg, for example from 50 to 2400 µg, from 50 to 2000 µg, from 50 to 1600 µg, from 50 to 800 µg, from 50 to 400 µg, from 50 to 200 µg, from 100 to 1600 µg, from 100 to 800 µg from 100 to 400 µg, from 100 to 200 µg, from 200 to 1600 µg, from 200 to 800 µg or from 200 to 400 µg, 100 to 400 µg being preferred. A suitable unit dose of monietasone furoate for inhalation may be from 25 to 2000 µg, for example from 50 µg to 1500 µg, from 50 to 1000 µg, from 50 to 800 µg, from 50 to 400 µg, from 50 to 200 µg, from 50 to 100 µg, from 100 to 800 µg, from 100 to 400 µg or from 100 to 200 µg, 100 to 400 µg being preferred. A suitable unit dose of fluticasone propionate for inhalation may be from 25 to 1000 µg, for example from 25 to 500 µg, from 25 to 250 µg, from 25 to 200 µg, from 50 to 1000 µg, from 50 to 500 µg, from 50 to 250 µg, from 50 to 200 µg, from 100 to 1000 µg, from 100 to 500 µg, from 100 to 250 µg, from 100 to 200 µg, from 150 to 500 µg or from 150 to 250 µg, 100 to 500 µg being preferred. These unit doses may be administered once or twice daily in accordance with the daily doses mentioned hereinbefore. The precise unit and daily dose used will of course depend on the condition to be treated, the patient and the efficiency of the inhalation device.

In one preferred embodiment of the invention, the medicament of the invention is a pharmaceutical composition which is a dry powder in a capsule containing a unit dose of (A) and (B), for example for inhalation from a single capsule inhaler, the capsule suitably containing a unit dose of (A) e.g. as hereinbefore described, and a unit dose of (B), e.g. as hereinbefore described, together with a pharmaceutically acceptable carrier as hereinbefore described in an amount to bring the total weight of dry powder per capsule to between 5 mg and 50 mg, for example 5 mg, 10 mg, 15 mg, 20 mg, 25 mg, 30 mg, 35 mg, 40 mg, 45 mg or 50 mg.

In another preferred embodiment of the invention, the medicament of the invention is a pharmaceutical composition which is a dry powder for administration from a reservoir of a multi-dose dry powder inhaler adapted to deliver, for example, 3 mg to 25 mg of powder containing a unit dose of (A) and (B) per actuation, for example, where (A) is in the form of the maleate salt, a powder comprising, by weight, 20 to 2000 parts, for example 60 to 1000 parts, 100 to 500 parts, or 100 to 300 parts of (A); 25 to 800 parts, e.g. 25 to 500 parts, 50 to 400 parts, or 100 to 400 parts of (B); and 2000 to 25000 parts, e.g. 4000 to 15000 parts or 4000 to 10000 parts of a pharmaceutically acceptable carrier as hereinbefore described.

In a further preferred embodiment of the invention, the medicament of the invention is a pharmaceutical composition which is an aerosol comprising (A) and (B), e g. in a ratio as hereinbefore described, in a propellant as hereinbefore described, optionally together with a surfactant and/or a bulking agent and/or a co-solvent such as ethanol as hereinbefore described, for administration from a metered dose inhaler adapted to deliver an amount of aerosol containing a unit dose of (A) and a unit dose of (B), or a known fraction of a unit dose of (A) and a known fraction of a unit dose of (B), per actuation. Thus if, for example, the inhaler delivers half of the unit doses of (A) and (B) per actuation, the unit doses can be administered by two actuations of the inhaler.

In accordance with the above, the invention also provides a pharmaceutical kit comprising (A) and (B) as hereinbefore defined in separate unit dosage forms, said forms being suitable for administration of (A) and (B) in effective amounts. Such a kit suitably further comprises one or more inhalation devices for administration of (A) and (B). For example, the kit may comprise one or more dry powder inhalation devices adapted to deliver dry powder from a capsule, together with capsules containing a dry powder comprising a dosage unit of (A) and capsules containing a dry powder comprising a dosage unit of (B). In another example, the kit may comprise a multidose dry powder inhalation device containing in the reservoir thereof a dry powder comprising (A) and a multidose dry powder inhalaiton device containing in the reservoir thereof a dry powder comprising (B). In a further example, the kit may comprise a metered dose inhaler containing an aerosol comprising comprising (A) in a propellant and a metered dose inhaler containing an aerosol comprising (B) in a propellant.

The medicaments of the invention are advantageous in the treatment of inflammatory or obstructive airways disease, exhibiting highly effective bronchodilatory and anti-inflammatory properties. For instance, it is possible using the combination therapy of the invention to reduce the dosages of corticosteroid required for a given therapeutic effect compared with those required using treatment with a corticosteroid alone, thereby minimising possibly undesirable side effects. In particular, these combinations, particularly where (A) and (B) are in the same composition, facilitate achievement of a high anti-inflammatory effect, such that the amount of corticosteroid needed for a given anti-inflammatory effect may be reduced when used in admixture with a compound of formula I, thereby reducing the risk of undesirable side effects from the repeated exposure to the steroid involved in the treatment of inflammatory or obstructive airways diseases. Furthermore, using the combinations of the invention, particularly using compositions containing (A) and (B), medicaments which have a rapid onset of action and a long duration of action may be prepared. Moreover, using such combination therapy, medicaments which result in a significant improvement in lung function may be prepared. In another aspect, using the combination therapy of the invention, medicaments which provide effective control of obstructive or inflammatory airways diseases, or a reduction in exacerbations of such diseases, may be prepared. In a further aspect, using compositions of the invention containing (A) and (B), medicaments which reduce or eliminate the need for treatment with short-acting rescue medicaments such as salbutamol or terbutaline, may be prepared; thus compositions of the invention containing (A) and (B) facilitate the treatment of an obstructive or inflammatory airways disease with a single medicament.

Treatment of inflammatory or obstructive airways diseases in accordance with the invention may be symptomatic or prophylactic treatment. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant form any previously administered symptomatic asthma therapy.

Other inflammatory or obstructive airways diseases and conditions to which the present invention is applicable include acute lung injury (AU), adult respiratory distress syndrome (ARDS), chronic obstructive pulmonary, airways or lung disease (COPD, COAD or COLD), including chronic bronchitis and emphysema, bronchiectasis and exacerbation of airways hyperreactivity consequent to other drug therapy, in particular other inhaled drug therapy. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tobacosis and byssinosis.

The invention is illustrated by the following Examples, in which parts are by weight unless stated otherwise. In the Examples, Compound A is the compound of formula I in the form of the maleate salt, Bud denotes budesonide, FP denotes fluticasone propionate, MF denotes mometasone furoate and OA denotes oleic acid (surfactant).

PREPARATION EXAMPLES

Preparation
1-3-chloro-1-(3,4-diethylphenyl)-1-proyanone 1,2-Diethylbenzene (10.9 g, 74.6 mmol) and propionyl chloride (9.7 g, 74.6 mmol) are added dropwise to $AlCl_3$ (22.3 g, 167.8 mmol) in nitromethane (75 mL) over 30 min. The reaction mixture is stirred at room temperature for 2 hours, after which 70 g of ice and 14 mL concentrated sulphuric acid are added. The aqueous phase is extracted with ether, and the combined organic phases extracted with 2N HCl and saturated aqueous NaCl. The organic phase is further treated with activated charcoal, magnesium sulphate, and filtered, and the solvent removed in vacuo.

1H-NMR ($CDCl_3$) ppm: 7.8 (1H, s, Ar); 7.7 (1H, d, Ar); 7.2 (1H, d, Ar); 3.9 (2H, t, $CH_2$); 3.4 (2H, t, $CH_2$); 2.8 (4H, q, $CH_2CH_3$); 1.2 (6H, m, $CH_3$).

Preparation 2-5,6-diethyl-indan-1-one 3-chloro-1-(3,4-diethylphenyl)-1-propanone (15.5 g) is dissolved in 66 mL concentrated sulphuric acid and heated to 90° C. for 4 hours. The reaction mixture is cooled, ice (70 g) is added, and the aqueous solution extracted twice with toluene. The organic layer is washed with sodium bicarbonate, saturated aqueous NaCl, and treated with activated charcoal and magnesium suphate. After filtration, the solvent is removed in vacuo. The product is purified by flash column chromatography (silica, hexane/ethylacetate 10:1), and further crystallised in hexane.

1H-NMR (CDCl3) ppm: 7.6 (1H, s, Ar); 7.3 (1H, d, Ar); 3.1 (2H, m, $CH_2$); 2.7 (6m, m, $CH_2+CH_2CH_3$); 1.2 (6, m, $CH_3$).

Preparation 3-5,6-Diethyl-indan-1,2-dione 2-oxime 5,6-diethyl-indan-1-one (5 g, 26 mmol) in methanol (75 mL) is brought to 40° C., n-butyl nitrite (3.0 g, 28.6 mmol) is added dropwise, followed by the addition of concentrated HCl (1.25 mL). After 1 hour, the reaction is brought to room temperature and the precipitated product filtered off, washed with ice-cold methanol and dried.

1H-NMR (d6-DMSO) ppm: 12.6 (1H, s, OH); 7.4 (1H, s, Ar); 7.3 (1H, d, Ar); 3.6 (2H, s, $CH_2$); 2.6 (4H, m, $CH_2CH_3$); 1.1 (6H, m, $CH_3$).

Preparation 4-5,6-Diethyl-indan-2-ylamine hydrochloride 5,6-Diethyl-indan-1,2-dione 2-oxime (4.5 g) is added to a mixture of acetic acid (150 mL), and concentrated sulphuric acid (4.5 mL). Pd/C 5% (1.5 g) is added, the reaction mixture degassed with nitrogen, and hydrogenated for 5 hours. The catalyst is then removed by filtration, the pH brought to pH 10 with 4M NaOH, and the solution errracted with chloroform. The organic phase is dried with magnesium sulphate, and the solvent removed in vacuo. The residue is redisolved in a minimum amount of ether, and HCl saturated ether added. The white precipitate is filtered and dried to yield the HCl salt of 5,6-diethyl-indan-2-ylamine.

1H-NMR (d6-DMSO) ppm: 8.7 (3H, bd s, $NH_3$); 7.3 (2H, s, Ar); 4.2 (1H, bd s, CH); 3.5 (2H, dd, $CH_2$); 3.3 (2H, dd, $CH_2$); 2.8 (4H, q, $CH_2CH_3$); 1.4 (6H, t, $CH_3$).

Preparation 5-8-benzyloxy-5-[(R)-2-(5,6-diethyl-indan-2-ylamino)-1-hydroxy-ethyl]-1H-quinolin-2-one A solution of (R)-8-benzyloxy-5-oxiranylcarbostyril (5.00 g) and 5,6-diethylindan-2-ylamine (3.87 g) in n-butanol is heated for 4 hours at 110° C. After cooling to room temperature toluene (100 ml) is added and the organic phase is washed with water (3×25 ml), loaded onto a silica gel chromatography column and eluted with toluene followed by a mixture of toluene:ethanol:ethyl acetate: conc. ammonia (45:10:45:2) to give the title compound.

Preparation 6—Compound A: 5-[(R)-2-(5,6-diethyl-indan-2-ylamino)-1-hydroxy-ethyl]-8-hydroxy-1H-quinolin-2-one maleate 8-benzyloxy-5-[(R)2-(5,6-diethyl-indan-2-ylamino)-1-hydroxy-ethyl]-1H-quinolin-2-one (360 mg) is dissolved in methanol (10 mL) and the compound is deprotected by adding a catalytic amount of 10% palladium on charcoal and placing the solution under an atmosphere of hydrogen. The reaction is shown to be complete by TLC after 4 hours. The catalyst is filtered off and the solvent is removed in vacuo. The product is taken up into isopropanol and a solution of maleic acid in isopropanol added. The title compound is obtained after recrystallisation from ethanol. TLC (silica, dichloromethane/methanol 10:1 $R_f$=0.05). ES+MS m/e 393 ($MH^+$).

Examples 1-60

Gelatin capsules suitable for use in a capsule inhaler such as that described in U.S. Pat. No. 3,991,761 are prepared, each capsule containing a dry powder obtained by mixing Compound A and budesonide which have been ground to a mean particle diameter of 1 to 5 μm and lactose monohydrate having a particle diameter below 212 μm, the amounts being as shown in the table below:

| Example | Compound A (Parts) | Budesonide (Parts) | Lactose (Parts) |
|---|---|---|---|
| 1 | 20 | 100 | 19880 |
| 2 | 40 | 100 | 19860 |
| 3 | 80 | 100 | 19820 |
| 4 | 100 | 100 | 19800 |
| 5 | 120 | 100 | 19780 |
| 6 | 140 | 100 | 19760 |
| 7 | 160 | 100 | 19740 |
| 8 | 180 | 100 | 19720 |
| 9 | 200 | 100 | 19700 |
| 10 | 220 | 100 | 19680 |
| 11 | 240 | 100 | 19660 |
| 12 | 300 | 100 | 19600 |
| 13 | 500 | 100 | 19400 |
| 14 | 1000 | 100 | 18900 |
| 15 | 2000 | 100 | 17900 |
| 16 | 20 | 100 | 24880 |
| 17 | 40 | 100 | 24860 |
| 18 | 80 | 100 | 24820 |
| 19 | 100 | 100 | 24800 |
| 20 | 120 | 100 | 24780 |
| 21 | 140 | 100 | 24760 |
| 22 | 160 | 100 | 24740 |
| 23 | 180 | 100 | 24720 |
| 24 | 200 | 100 | 24700 |
| 25 | 220 | 100 | 24680 |
| 26 | 240 | 100 | 24660 |
| 27 | 300 | 100 | 24600 |
| 28 | 500 | 100 | 24400 |
| 29 | 1000 | 100 | 23900 |
| 30 | 2000 | 100 | 22900 |
| 31 | 20 | 200 | 14780 |
| 32 | 40 | 200 | 14760 |
| 33 | 80 | 200 | 14720 |
| 34 | 100 | 200 | 14700 |
| 35 | 120 | 200 | 14680 |
| 36 | 140 | 200 | 14660 |
| 37 | 160 | 200 | 14640 |
| 38 | 180 | 200 | 14620 |
| 39 | 200 | 200 | 14600 |
| 40 | 220 | 200 | 14580 |
| 41 | 240 | 200 | 14560 |
| 42 | 300 | 200 | 14500 |
| 43 | 500 | 200 | 14300 |
| 44 | 1000 | 200 | 13800 |
| 45 | 2000 | 200 | 12800 |
| 46 | 20 | 200 | 24780 |
| 47 | 40 | 200 | 24760 |
| 48 | 80 | 200 | 24720 |
| 49 | 100 | 200 | 24700 |
| 50 | 120 | 200 | 24680 |
| 51 | 140 | 200 | 24660 |
| 52 | 160 | 200 | 24640 |
| 53 | 180 | 200 | 24620 |
| 54 | 200 | 200 | 24600 |
| 55 | 220 | 200 | 24580 |
| 56 | 240 | 200 | 24560 |
| 57 | 300 | 200 | 24500 |
| 58 | 500 | 200 | 24300 |
| 59 | 1000 | 200 | 23800 |
| 60 | 2000 | 200 | 22800 |

Examples 61-90

Examples 1-60 are repeated, but replacing the budesonide by mometasone furoate, and using amounts as shown in the following table:

| Example | Compound A (Parts) | MF (Parts) | Lactose (Parts) |
|---|---|---|---|
| 61 | 20 | 100 | 24880 |
| 62 | 40 | 100 | 24860 |
| 63 | 80 | 100 | 24820 |
| 64 | 100 | 100 | 24800 |
| 65 | 120 | 100 | 24780 |
| 66 | 140 | 100 | 24760 |
| 67 | 160 | 100 | 24740 |
| 68 | 180 | 100 | 24720 |
| 69 | 200 | 100 | 24700 |
| 70 | 220 | 100 | 24680 |
| 71 | 240 | 100 | 24660 |
| 72 | 300 | 100 | 24600 |
| 73 | 500 | 100 | 24400 |
| 74 | 1000 | 100 | 23900 |
| 75 | 2000 | 100 | 22900 |
| 76 | 20 | 200 | 14780 |
| 77 | 40 | 200 | 14760 |
| 78 | 80 | 200 | 14720 |
| 79 | 100 | 200 | 14700 |
| 80 | 120 | 200 | 14680 |
| 81 | 140 | 200 | 14660 |
| 82 | 160 | 200 | 14640 |
| 83 | 180 | 200 | 14620 |
| 84 | 200 | 200 | 14600 |
| 85 | 220 | 200 | 14580 |
| 86 | 240 | 200 | 14560 |
| 87 | 300 | 200 | 14500 |
| 88 | 500 | 200 | 14300 |
| 89 | 1000 | 200 | 13800 |
| 90 | 2000 | 200 | 12800 |

Examples 91-135

A dry powder suitable for delivery from the reservoir of the multi-dose inhaler described in WO97/10589 is prepared by mixing Compound A and fluticasone propionate which have been ground to a mean particle diameter of 1-5 μm and lactose monohydrate having a particle diameter below 212 μm, the amounts being as shown in the table below

| Example | Compound A (Parts) | FP (Parts) | Lactose (Parts) |
|---|---|---|---|
| 91 | 20 | 100 | 4880 |
| 92 | 40 | 100 | 4860 |
| 93 | 80 | 100 | 4820 |
| 94 | 100 | 100 | 4800 |
| 95 | 120 | 100 | 4780 |
| 96 | 140 | 100 | 4760 |
| 97 | 160 | 100 | 4740 |
| 98 | 180 | 100 | 4720 |
| 99 | 200 | 100 | 4700 |
| 100 | 220 | 100 | 4680 |
| 101 | 240 | 100 | 4660 |
| 102 | 300 | 100 | 4600 |
| 103 | 500 | 100 | 4400 |
| 104 | 1000 | 100 | 3900 |
| 105 | 2000 | 100 | 2900 |
| 106 | 20 | 200 | 9780 |
| 107 | 40 | 200 | 9760 |
| 108 | 80 | 200 | 9720 |
| 109 | 100 | 200 | 9700 |
| 110 | 120 | 200 | 9680 |
| 111 | 140 | 200 | 9660 |
| 112 | 160 | 200 | 9640 |
| 113 | 180 | 200 | 9620 |
| 114 | 200 | 200 | 9600 |
| 115 | 220 | 200 | 9580 |
| 116 | 240 | 200 | 9560 |
| 117 | 300 | 200 | 9500 |
| 118 | 500 | 200 | 9300 |
| 119 | 1000 | 200 | 8800 |
| 120 | 2000 | 200 | 7800 |
| 121 | 20 | 250 | 14730 |
| 122 | 40 | 250 | 14710 |
| 123 | 80 | 250 | 14670 |
| 124 | 100 | 250 | 14650 |
| 125 | 120 | 250 | 14630 |
| 126 | 140 | 250 | 14610 |
| 127 | 160 | 250 | 14590 |
| 128 | 180 | 250 | 14570 |
| 129 | 200 | 250 | 14550 |
| 130 | 220 | 250 | 14530 |
| 131 | 240 | 250 | 14510 |
| 132 | 300 | 250 | 14450 |
| 133 | 500 | 250 | 14250 |
| 134 | 1000 | 250 | 13750 |
| 135 | 2000 | 250 | 12750 |

Examples 136-163

Aerosol formulations are prepared by dispensing micronised active ingredients and, if required, lactose as bulking agent into a vial, sealing the vial with a metering valve, injecting the premixed ethanol/propellant and optional surfactant into the vial through the valve and subjecting the vial to, ultrasonic energy to disperse the solid particles. The components and amounts used are shown in the following tables:

| Ex. | Cpd.A (Parts) | MF (Parts) | HFA134a (Parts) | HFA227 (Parts) | Ethanol (Parts) | OA (Parts) | Lactose (Parts) |
|---|---|---|---|---|---|---|---|
| 136 | 2 | 10 | 36500 | 60750 | 2500 | — | 70 |
| 137 | 4 | 10 | 3410 | 6340 | 230 | 0.3 | — |
| 138 | 8 | 10 | 97000 | — | 2500 | — | 90 |
| 139 | 10 | 10 | 30500 | 67000 | 2500 | 0.5 | 100 |
| 140 | 12 | 10 | 3150 | 6550 | 250 | 1 | — |
| 141 | 14 | 10 | 3700 | 6050 | 250 | 0.8 | — |
| 142 | 16 | 10 | 3800 | 5900 | 230 | 0.4 | — |
| 143 | 18 | 10 | 4700 | 5050 | 250 | 1 | — |
| 144 | 20 | 20 | 3600 | 6150 | 225 | 1 | — |
| 145 | 22 | 20 | 3500 | 6200 | 230 | 1 | — |
| 146 | 24 | 20 | 98000 | — | 2500 | 1 | — |
| 147 | 30 | 20 | 3900 | 5900 | 250 | 1 | — |
| 148 | 2 | 20 | 30000 | 67000 | 2250 | 0.2 | 90 |
| 149 | 10 | 20 | 3500 | 6200 | 250 | 0.5 | — |
| 150 | 14 | 20 | 3200 | 6500 | 230 | 1 | — |

-continued

| Ex. | Cpd.A (Parts) | HFA134a (Parts) | HFA227 (Parts) | Ethanol (Parts) | OA (Parts) | Lactose (Parts) |
|---|---|---|---|---|---|---|
| 151 | 18 | 20 | 3100 | 6200 | 225 | 0.8 | — |
| 152 | 20 | 20 | 3150 | 6100 | 225 | 1 | — |
| 153 | 24 | 20 | 30000 | 60000 | 2000 | 0.8 | — |

| Ex. | Cpd.A (Parts) | FP (Parts) | HFA134a (Parts) | HFA227 (Parts) | Ethanol (Parts) | OA (Parts) | Lactose (Parts) |
|---|---|---|---|---|---|---|---|
| 154 | 4 | 10 | 34000 | 63000 | 2250 | 0.3 | 50 |
| 155 | 8 | 10 | 92000 | — | 2500 | 0.5 | 70 |
| 156 | 12 | 10 | 3000 | 5500 | 200 | — | — |
| 157 | 16 | 10 | 2500 | 5000 | 200 | 0.3 | — |
| 158 | 20 | 10 | 2000 | 3000 | 150 | 0.2 | — |
| 159 | 30 | 10 | 2000 | 2000 | 150 | 0.2 | — |
| 160 | 8 | 20 | 20000 | 25000 | 1500 | 0.2 | — |
| 161 | 12 | 20 | 2500 | 2500 | 200 | 0.2 | — |
| 162 | 20 | 20 | 2000 | 2000 | 150 | 0.2 | — |
| 163 | 30 | 20 | 20000 | 20000 | 1500 | 0.2 | — |

Examples 164-199

The procedure of Examples 91-135 is repeated, but replacing fluticasone propionate by mometasone furoate, and using amounts as shown in the following table.

| Example | Compound A (Parts) | MF (Parts) | Lactose (Parts) |
|---|---|---|---|
| 164 | 100 | 100 | 4800 |
| 165 | 200 | 100 | 4700 |
| 166 | 300 | 100 | 4600 |
| 167 | 400 | 100 | 4500 |
| 168 | 500 | 100 | 4400 |
| 169 | 600 | 100 | 4300 |
| 170 | 700 | 100 | 4200 |
| 171 | 800 | 100 | 4100 |
| 172 | 2000 | 100 | 2900 |
| 173 | 100 | 200 | 4700 |
| 174 | 200 | 200 | 4600 |
| 175 | 300 | 200 | 4500 |
| 176 | 400 | 200 | 4400 |
| 177 | 500 | 200 | 4300 |
| 178 | 600 | 200 | 4200 |
| 179 | 700 | 200 | 4100 |
| 180 | 800 | 200 | 4000 |
| 181 | 1200 | 200 | 3600 |
| 182 | 100 | 400 | 4500 |
| 183 | 200 | 400 | 4400 |
| 184 | 300 | 400 | 4300 |
| 185 | 400 | 400 | 4200 |
| 186 | 500 | 400 | 4100 |
| 187 | 600 | 400 | 4000 |
| 188 | 700 | 400 | 3900 |
| 189 | 800 | 400 | 3800 |
| 190 | 100 | 100 | 9800 |
| 191 | 200 | 100 | 9700 |
| 192 | 300 | 100 | 9600 |
| 193 | 400 | 100 | 9500 |
| 194 | 500 | 100 | 9400 |
| 195 | 100 | 200 | 9700 |
| 196 | 200 | 200 | 9600 |
| 197 | 300 | 200 | 9500 |
| 198 | 400 | 200 | 9400 |
| 199 | 500 | 200 | 9300 |

Examples 200-236

The procedures of Examples 136-163 is repeated, but using the amounts shown in the following table, the ethanol being omitted in some of the Examples:

| Ex. | Cpd.A (Parts) | MF (Parts) | HFA134a (Parts) | HFA227 (Parts) | Ethanol (Parts) | OA (Parts) | Lactose (Parts) |
|---|---|---|---|---|---|---|---|
| 200 | 20 | 20 | 5000 | — | 200 | 0.5 | — |
| 201 | 40 | 2 | 2500 | 2500 | — | — | — |
| 202 | 75 | 25 | 1500 | 3500 | 500 | — | 1 |
| 203 | 20 | 20 | 3600 | 6150 | 225 | — | 0.5 |
| 204 | 2 | 20 | 30000 | 67000 | — | — | — |
| 205 | 14 | 20 | 3200 | 6500 | 1500 | — | 4 |
| 206 | 20 | 20 | 3150 | 6100 | 1500 | 4 | — |
| 207 | 10 | 20 | 4700 | 5050 | 500 | — | 0.2 |
| 208 | 60 | 20 | 10000 | 10000 | — | — | — |
| 209 | 60 | 20 | 10000 | 10000 | 200 | — | — |
| 210 | 60 | 20 | 10000 | 10000 | — | 0.5 | — |
| 211 | 30 | 20 | 8000 | 12000 | — | 1 | 1 |
| 212 | 40 | 20 | 5000 | 15000 | 500 | 0.5 | 0.5 |
| 213 | 50 | 20 | 9000 | 11000 | 400 | 0.8 | 0.2 |
| 214 | 20 | 20 | 4600 | 5000 | 400 | 0.4 | 0.2 |
| 215 | 30 | 10 | 20000 | 25000 | — | — | — |

-continued

| Ex. | Cpd.A (Parts) | HFA134a (Parts) | HFA227 (Parts) | Ethanol (Parts) | OA (Parts) | Lactose (Parts) |
|---|---|---|---|---|---|---|
| 216 | 40 | 10 | 20000 | 30000 | — | — |
| 217 | 60 | 10 | 35000 | 65000 | — | — |

| Ex. | Cpd.A (Parts) | FP (Parts) | HFA134a (Parts) | HFA227 (Parts) | Ethanol (Parts) | OA (Parts) | Lactose (Parts) |
|---|---|---|---|---|---|---|---|
| 218 | 20 | 10 | 5000 | 5000 | — | — | 1 |
| 219 | 10 | 10 | 3650 | 6350 | — | — | 1 |
| 220 | 30 | 10 | 3200 | 6800 | 100 | 0.5 | 0.5 |
| 221 | 30 | 20 | 7400 | 7600 | 100 | — | — |
| 222 | 40 | 20 | 8300 | 6700 | 200 | 0.5 | — |
| 223 | 60 | 20 | 3100 | 6900 | 300 | 1 | — |
| 224 | 10 | 10 | 8000 | 12000 | — | — | — |
| 225 | 50 | 20 | 1600 | 3400 | 500 | 2 | 0.5 |

| Ex. | Cpd.A (Parts) | Bud (Parts) | HFA134a (Parts) | HFA227 (Parts) | Ethanol (Parts) | OA (Parts) | Lactose (Parts) |
|---|---|---|---|---|---|---|---|
| 226 | 10 | 20 | 5500 | 4500 | — | — | — |
| 227 | 2 | 20 | 3500 | 6500 | — | — | 1 |
| 228 | 1 | 20 | 2500 | 7500 | — | — | 1 |
| 229 | 20 | 20 | 3800 | 6100 | 100 | 0.5 | — |
| 230 | 15 | 20 | 3300 | 6600 | 100 | 0.5 | 0.5 |
| 231 | 30 | 20 | 3600 | 5900 | 500 | 4 | — |
| 232 | 40 | 20 | 4600 | 4900 | 500 | 3 | — |
| 233 | 30 | 10 | 3100 | 6800 | 100 | 0.2 | 0.5 |
| 234 | 40 | 10 | 1400 | 3100 | 500 | 0.2 | — |
| 235 | 60 | 10 | 8000 | 12000 | — | — | 1 |
| 236 | 80 | 10 | 30000 | 70000 | — | — | — |

Example 237-245

The procedure of Examples 136-163 is repeated, but using sorbitan trioleate (ST) as surfactant in place of oleic acid, the amounts of the ingredients being as shown in the following table:

| Ex. | Cpd.A (Parts) | MF (Parts) | HFA134a (Parts) | HFA227 (Parts) | Ethanol (Parts) | ST (Parts) | Lactose (Parts) |
|---|---|---|---|---|---|---|---|
| 237 | 60 | 40 | 10000 | 10000 | 300 | 4 | — |
| 238 | 60 | 20 | 8000 | 12000 | 200 | 8 | — |
| 239 | 50 | 20 | 12000 | 8000 | 400 | 10 | — |
| 240 | 40 | 20 | 5000 | 5000 | 600 | 2.5 | 1 |
| 241 | 30 | 20 | 3500 | 6500 | — | 4 | 2 |
| 242 | 20 | 20 | 6000 | 4000 | — | 3 | 3 |
| 243 | 10 | 20 | 4500 | 5500 | 100 | 2 | 1 |
| 244 | 20 | 10 | 4100 | 5900 | 50 | 1 | 2 |
| 245 | 15 | 5 | 1550 | 3450 | 200 | 0.5 | 1 |

The invention claimed is:

1. A pharmaceutical composition comprising,
(a) a compound

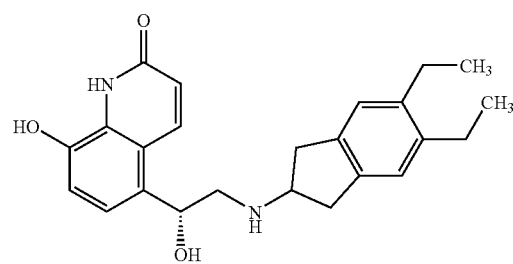

(I)

in free or pharmaceutically acceptable salt; and (b) mometasone furoate, for simultaneous administration in the treatment of an inflammatory or obstructive airways disease, the molar ratio of (a) to (b) being from 3:1 to 1:7 and a pharmaceutically acceptable carrier; which is in inhalable form and is:
 (i) an aerosol comprising a mixture of (a) and (b) in solution or dispersion in a propellant;
 (ii) a combination of an aerosol containing (a) in solution or dispersion in a propellant with an aerosol containing (b) in solution or dispersion in a propellant;
 (iii) a nebulizable composition comprising a dispersion of (a) and (b) in an aqueous, organic or aqueous/organic medium; or
 (iv) a combination of a dispersion of (a) in an aqueous, organic or aqueous/organic medium with a dispersion of (b) in an aqueous, organic or aqueous/organic medium.

2. The pharmaceutical composition according to claim 1, in which (a) or (b), or (a) and (b), are present in inhalable form as a dry powder comprising respectively finely divided (a) or (b), or finely divided (a) and (b), optionally together with at least one particulate pharmaceutically acceptable carrier.

3. The pharmaceutical composition according to claim 1, in which (a) or (b), or (a) and (b), has an average particle diameter up to 10 μm.

4. The pharmaceutical composition according to claim 2, in which (a) or (b), or (a) and (b), has an average particle diameter up to 10 μm.

5. The pharmaceutical composition according to claim 1, in which the molar ratio of (a) to (b) is from 2:1 to 1:2.

6. The pharmaceutical composition according to claim 2, which is a dry powder in a capsule, the capsule containing a unit dose of (a), a unit dose of (b) and a pharmaceutically acceptable carrier in an amount to bring the total weight of dry powder per capsule to between 5 mg and 50 mg.

7. The pharmaceutical composition according to claim 2, which is a dry powder comprising, by weight, from 20 to 2000 parts of (a) in the form of the maleate salt, from 25 to 800 parts of (b) and 2000 to 25000 parts of a pharmaceutically acceptable carrier.

8. The pharmaceutical composition according to claim 2, which is an aerosol comprising (a) and (b), the molar ratio of (a) to (b) being from 3:1 to 1:7, in a propellant, optionally together with one or more components selected from a surfactant, a bulking agent and a co-solvent, suitable for administration from a metered dose inhaler adapted to deliver an amount of aerosol containing a unit dose of (a) and a unit dose of (b), or a known fraction of a unit dose of (a) and a known fraction of a unit dose of (b), per actuation.

* * * * *